United States Patent
Wolfe

[11] Patent Number: 5,235,987
[45] Date of Patent: Aug. 17, 1993

[54] NEEDLE GUIDE
[75] Inventor: Jerome K. Wolfe, Export, Pa.
[73] Assignee: Dymax Corporation, Pittsburgh, Pa.
[21] Appl. No.: 857,095
[22] Filed: Mar. 20, 1992

Related U.S. Application Data
[63] Continuation of Ser. No. 660,441, Feb. 22, 1991, abandoned.

[51] Int. Cl.[5] .............................................. A61B 8/12
[52] U.S. Cl. ................................. 128/662.05; 128/754; 604/16
[58] Field of Search .................... 128/660.01, 662.05, 128/662.06, 754; 604/16

[56] References Cited

U.S. PATENT DOCUMENTS

| 4,108,165 | 8/1978  | Kopp et al.    | 128/662.05 |
| 4,402,324 | 9/1983  | Lindgren et al.| 128/662.05 |
| 4,408,611 | 10/1983 | Enjoji         | 128/662.05 |
| 4,548,210 | 10/1985 | Enjoji et al.  | 128/662.05 |
| 4,576,175 | 3/1986  | Epstein        | 128/662.05 |
| 4,635,644 | 1/1987  | Yagata         | 128/662.05 |
| 4,742,829 | 5/1988  | Law et al.     | 128/662.05 |
| 4,898,178 | 2/1990  | Wedel          | 128/662.05 |
| 4,899,756 | 2/1990  | Sonek          | 128/662.05 |
| 4,911,173 | 3/1990  | Terwilliger    | 128/662.06 |

FOREIGN PATENT DOCUMENTS
8403034  8/1984  PCT Int'l Appl. ............ 128/662.05

Primary Examiner—Kyle L. Howell
Assistant Examiner—George Manuel
Attorney, Agent, or Firm—Ansel M. Schwartz

[57] ABSTRACT

A one-piece needle guide for use with a medical ultrasonic scanning apparatus to guide a needle. The needle guide includes a body which is adapted to be releasably secured to the scanning apparatus. A tubular channel extends the length of the body on its upper surface. The channel is for engaging and guiding the needle in proper alignment with the scanning apparatus. A pair of flexible lips form the shape of the channel and are adapted to secure the needle in a slidable manner. The flexibility of the lips allow the needle to be removed from the body.

6 Claims, 1 Drawing Sheet

NEEDLE GUIDE

This is a continuation of copending application Ser. No. 07/660,441, filed on Feb. 22, 1991, now abandoned.

FIELD OF THE INVENTION

The present invention relates to a needle guide for use with a medical ultrasonic scanning apparatus. In particular, the present invention is a disposable one-piece needle guide in which the needle can be disengaged from the needle guide in a simple fashion.

BACKGROUND OF THE INVENTION

Ultrasonic scanners are commonly used in medical diagnostic testing to produce a two dimensional, cross sectional image of the body region being scanned. Needle guides have been releasably attached to ultrasonic scanners to orient a needle within a specific internal body part, such as a vein or artery. In such cases, the needle guide serves to axially align the tip of the needle within the scan plane at the focal zone of the ultrasonic scanner, so as the cross sectional image produced by the scanner reveals the tip of the needle in relationship to the internal body parts.

Numerous needle guides of various construction have been proposed. Amedic, Inc. of Phoenix, Ariz. manufactures a two part disposable needle guide with a groove extending along its length. A pivoting member covers the groove to secure the needle within the groove. There is no teaching to use a one-piece needle guide to perform the same function. U.S. Pat. No. 4,883,059 to Stedman describes a two part needle guide consisting of a grooved member and a cover to enclose the groove. U.S. Pat. No. 4,838,500 to Cooper describes an alternative construction of a two part needle guide. U.S. Pat. No. 4,469,106 to Harvi describes a needle guide with numerous interconnected members. None, however, describe a one-piece needle guide construction which guides and aligns the needle in a linear path at a predetermined angle with respect to the ultrasonic scanner, while also allowing the needle to be separated from the guide.

SUMMARY OF THE INVENTION

The present invention pertains to a one-piece needle guide for use with a medial ultrasonic scanning apparatus to guide a needle. The needle guide includes a body which is adapted to be releasably secured to the scanning apparatus. A tubular channel extends the length of the body on its upper surface. The channel is for engaging and guiding the needle in proper alignment with the scanning apparatus. A pair of flexible lips form the shape of the channel and are adapted to secure the needle in a slidable manner. The flexibility of the lips allow the needle to be removed from the guide.

BRIEF DESCRIPTION OF THE DRAWINGS

In the accompanying drawings, the preferred embodiments of the invention and preferred methods of practicing the invention are illustrated in which.

DESCRIPTION OF THE PREFERRED EMBODIMENT

Figure 1:
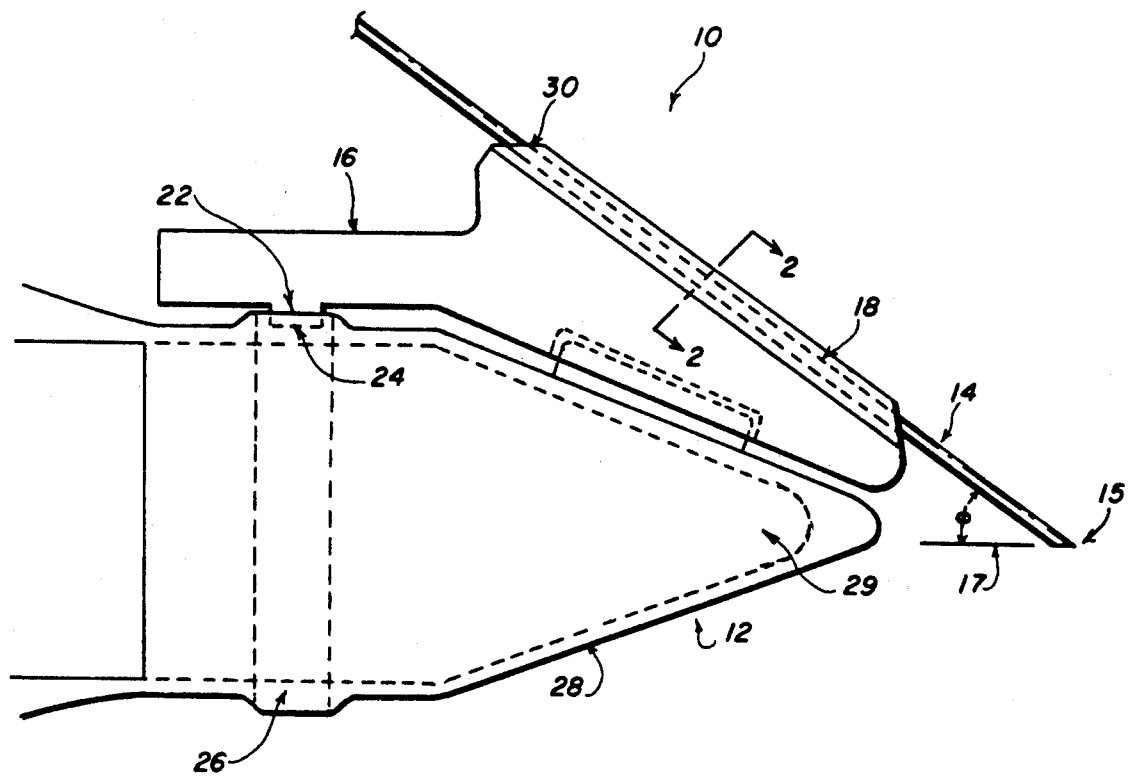
FIG. 1 is a side view of the needle guide engaged with the ultrasonic scanning device.

Referring now to the drawings wherein like reference numerals refer to similar or identical parts throughout the several views, and more specifically to FIG. 1 thereof, there is shown a needle guide 10 for use with a medical ultrasonic scanning apparatus 12 to guide a needle 14 of a specific diameter. The needle guide 10 is preferably of one-piece construction having a body 16 which is adapted to be releasably secured to the ultrasonic scanning apparatus 12. The needle guide 10 can be sterile and disposable.

Figure 2:
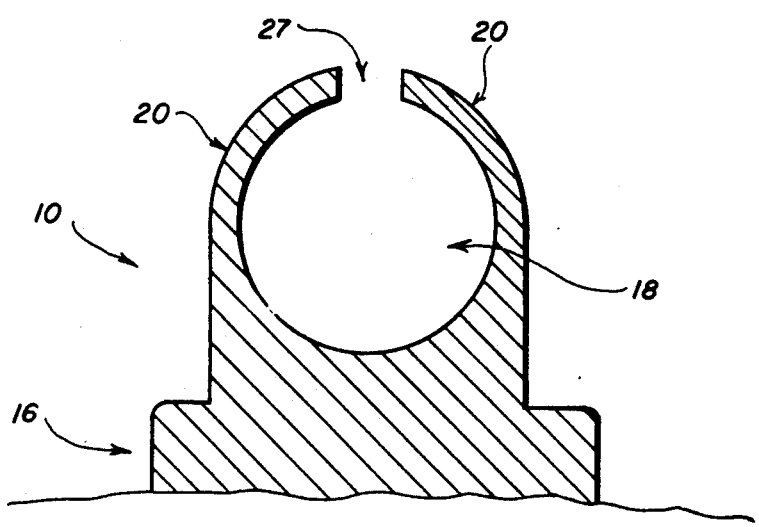
FIG. 2 is a cross section of the tubular channel of the needle guide.

A tubular channel 18 extends along the length of the body 16 for engaging and guiding the needle 14 into proper alignment with the ultrasonic scanning apparatus 12. Preferably, the guide 10 aligns the needle 14 being inserted into a patient such that the needle tip 15 converges on the scan plane at the focal zone of the crystal (not shown) of the apparatus 12. A particular advantage of the present needle guide 10 over the prior art is that the tubular channel 18 is formed by flexible lips 20 which are adapted to secure the needle 14 onto the body 16 in a slidable manner as shown in FIG. 2. The flexible nature of the lips 20 allows the needle 14 to be removed from the body 16. The flexibility of the lips 20 can be varied by changing their thickness or the material from which the guide is made.

In a more preferred embodiment, the needle guide 10 is comprised of a single piece of molded plastic. Preferably, a high density medical grade plastic is used such as high density polyethylene (HDPE). The body 16 preferably comprises a keyed portion 22 which is adapted to engage and lock with a notch 24 formed on the scanning apparatus 12. Preferably, the notch is formed on a locking ring 26. A disposable sheath 28 is commonly used to sterilly cover the scanning head 29 of the ultrasonic scanning apparatus 12 and also covers the ring 26. The needle guide 10 preferably locks with the notch 24 such that the sheath 28 is between the notch 24 and the guide 10. However, any convenient means to releasably attach the needle guide 10 to the ultrasonic scanning apparatus 12 can be used.

The tubular channel 18 is formed from flexible lips 20 which substantially encompass the needle 14 to guide the needle 14 in proper alignment with the ultrasonic scanning apparatus 12. Preferably, the channel 18 has a circular cross section except for an axial slit 27. The channel 18 preferably forms an angle $\phi$ with the plane 17 produced by the crystal of the apparatus 12 such that the needle converges on the scan plane at the focal zone of the crystal.

The axial slit 28 allows the needle 14 to be disengaged from the needle guide 10 by pulling the needle 14 away from the scanning apparatus 12 and through the axial slit 27. The diameter of the channel 18 is toleranced to encompass a needle 14 of specific diameter. Needle guides 10 with channels 18 of various predetermined diameters could be available to accommodate the various sizes of needles 14, for instance, with respect to pediatric or adult sizes. The lips 20 are preferably constructed with flared ends 30 which allows the needle to be easily inserted into the tubular channel 18.

There can be a plurality of needle guides 10, each having a unique angle $\phi$, to correspond with different focal zones of different crystals. Crystals with shorter focal length require needle guides 10 with larger angles $\phi$. Crystals with longer focal lengths require guides 10 with smaller angles φ. The choice of the crystal of the apparatus 12 is to an extent dependent on the proximity of the area to be scanned in the patient with the skin surface of the patient. Thus, depending on the crystal and needle 14 size, a desired needle guide 10 can be chosen from a packet of needle guides 10 with different size channels 18 or different angles φ. The angle φ can vary according to the circumstances and the application. The angle φ can be very small so the needle, as it moves, is essentially in parallel with the scan plane of the apparatus 12; or very large so the needle, as it moves, is essentially perpendicular with the scan plane of the apparatus 12.

In the operation of the present invention, the needle guide 10 having a desired angle with respect to the focal zone of the crystal in the probe 12 is attached to the ultrasonic scanning apparatus 12 by engaging the key portion 22 of the guide 10 with the notch 24 of the locking ring 26. The needle 14 is placed into the tubular channel 18. Flared end 30 facilitates the introduction of the needle 14 into the channel 18. The ultrasonic scanning apparatus 12 is then positioned to reveal the desired cross section of the patient. When a preferable region is imaged, the needle 14 is slid through the channel 18 and into the portion of the body which is to be punctured.

Once the needle 14 is in the appropriate position as seen by the scanning apparatus 12, the needle guide 10 and thus the scanning apparatus 12 can be separated from the needle 14. This is easily accomplished by supporting the needle 14 within the patient while simultaneously pulling the ultrasonic scanning apparatus away from the needle. The flexible nature of the lips 20 allows them to deflect outward thereby releasing the needle 14 from their grasp. The needle guide 10 and the sheath 28 can then be disposed of, and a new sterile needle guide having the proper angle with respect to the focal zone of the crystal in the apparatus 12 along with a new sterile sheath 28 can be attached thereto for the next patient.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. A needle guiding system for guiding a needle of a specific diameter into a patient comprising:
    an ultrasonic scanning apparatus having a scan plane and a focal zone in the scan plane; and
    a needle guide having a body releasably secured to the scanning apparatus having a tubular channel extending essentially the length of the body for engaging and guiding the needle into proper alignment with the scanning apparatus, a needle free-standing within the tubular channel and said tubular channel having flexible lips defining a longitudinal slot slidingly holding said needle within the tubular channel which forms an angle with the scan plane of the ultrasonic scanning apparatus such that the needle when in the patient is caused to converge on the scan plane at the focal zone of the apparatus, said flexible lips secure the needle onto the body in a slidable manner while allowing the needle to be separated from the body through the slot while the body is attached to the scanning apparatus.

2. A needle guide as described in claim 1 wherein the channel defines flared ends which allow the needle to be inserted into the channel.

3. A needle guide as described in claim 2 wherein the body comprises means for being releasably secured to the ultrasonic scanning apparatus with a disposable sheath between the scanning apparatus and the body.

4. A needle guide as described in claim 3 wherein the body comprises a keyed portion adapted to engage with a notch formed on the scanning device.

5. A needle guide as described in claim 4 comprised of a single piece of molded plastic.

6. A needle guide as described in claim 5 wherein the channel forms an angle with the focal zone of the crystal of the ultrasonic scanning apparatus such that the needle when in the patient is caused to converge on the focal zone of the crystal by passing inside the scan plane.

* * * * *